US006700004B2

(12) United States Patent
Geller et al.

(10) Patent No.: US 6,700,004 B2
(45) Date of Patent: Mar. 2, 2004

(54) POLYAMINO ACID-CATALYZED PROCESS FOR THE ENANTIOSELECTIVE EPOXIDATION OF α,β-UNSATURATED ENONES AND α,β-UNSATURATED SULFONES

(75) Inventors: Thomas Geller, Odenthal (DE); Christa Maria Krüger, Münster (DE); Hans-Christian Militzer, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 28 days.

(21) Appl. No.: 10/201,881

(22) Filed: Jul. 24, 2002

(65) Prior Publication Data

US 2003/0064486 A1 Apr. 3, 2003

(30) Foreign Application Priority Data

Jul. 27, 2001 (DE) .......................................... 101 36 485

(51) Int. Cl.$^7$ ...................... C07D 301/03; C07D 301/12
(52) U.S. Cl. ......................... 549/524; 549/531; 549/535
(58) Field of Search ................................ 549/524, 531, 549/535

(56) References Cited

U.S. PATENT DOCUMENTS

| 6,225,482 B1 | | 5/2001 | Drauz et al. ................. 549/525 |
| 6,348,608 B1 | * | 2/2002 | Shi ............................. 549/524 |
| 6,409,769 B1 | | 6/2002 | Shi ............................. 649/519 |
| 6,495,725 B2 | * | 12/2002 | Ogasawara .................. 568/338 |
| 6,541,475 B2 | * | 4/2003 | Reddy et al. ........... 514/252.12 |
| 6,559,283 B2 | * | 5/2003 | Drauz et al. ................. 530/332 |
| 2002/0133031 A1 | | 9/2002 | Shi ............................. 549/524 |

FOREIGN PATENT DOCUMENTS

| EP | 0 403 252 | 12/1990 |
| EP | 1 006 111 | 6/2000 |
| WO | 96/33183 | 10/1996 |

OTHER PUBLICATIONS

Bioorganic & Medicinal Chemistry, 7, 1999, pp. 2145–2156, "Polyamino Acids as Catalysts in Asymmetric Synthesis" by M. J. Porter, S. M. Roberts, and J. Skidmore.
Tedrahedron Letters, 40, 1999, pp. 5421–5424, PaaSicats: Powerful Catalysts for Asymmetric Epoxidation of Enones. Novel Syntheses of α–Arylpropanoic Acids including (S)–Fenoprofen by L. Carde, H. Davies, T.–P. Geller and S. M. Roberts.
Tetrahedron Letters, 39, 1998, pp. 7353–7356, "Water vs. Desiccant. Improvement of Yb–BINOL Complex Catalyzed Enantioselective Epoxidation of Enones" by S. Watanabe, Y. Kobayashi, T. Arai, H. Sasai, M. Bougauchi, and M. Shibasaki.

Tetrahedron Letters, 39, 1998, pp. 1599–1602, "Asymmetric Phase–Transfer Mediated Epoxidation of α, β–Unsaturated Ketones Using Catalysts Derived From *Cinchona* Alkaloids" by B. Lygo and P. G. Wainwright.
Tetrahedron Letters, No. 21, pp. 1831–1834, 1976, "Catalytic Asymmetric Induction in Oxidation Reactions. The Synthesis of Optically Active Epoxides." by R. Helder, J. C. Hummelen, R. W. P. M. Laane, J. S. Wiering and H. Wynberg.
Tetrahedron Letters, 39, 1998, pp. 7563–7566, "Asymmetric Epoxidation of α,β–Unsaturated Ketones Under Phase–Transfer Catalyzed Conditions" by S. Arai, H. Tsuge and T. Shioiri.
Tetrahedron Letters, 39, 1998, pp. 7321–7322, "Remarkable Ligand Effect on the Enantioselectivity of the Chiral Lanthanum Complex–Catalyzed Asymmetric Epoxidation of Enones" by K. Daikai, M. Kamaura, and J. Inanaga.
Agnew. Chem. Int. Ed. Engl., 1997, 36, No. 4, pp. 410–412, "Asymmetric Expoxidation of Chalcones with Chirally Modified Lithium and Magnesium tert–Butyl Peroxides" by C. L. Elston, R. F. W. Jackson, S. J. F. MacDonald and P. J. Murray.
Liebigs Ann/Recueil, 1997, pp. 1101–1113, "Zinc–Mediated Asymmetric Epoxidation of α–Enones" by D. Enders, J. Zhu, and L. Kramps.
Tedrahedron Letters 40, 1999, pp. 5207–5210, "cis–Selective Aziridination of cis– or trans–α,β–Unsaturated Amides Using Diaziridine" by K. Hori, H. Sugihara, Y. N. Ito and T. Katsuki.
J. Chem. Soc., Perkin Trans. I, 1982, pp. 1317–1324, "Synthetic Enzymes. Part 2. Catalytic Asymmetric Epoxidation by means of Polyamino–acids in a Triphase System" by S. Juliá, J. Guixer, J. Masana and J. Rocas.
Org. Synth. Mod. Trends. Proc. 1UPAC Symp., 6$^{th}$, 1986, pp. 275–284, "Asymmetric syntheses catalyzed by natural and synthetic peptides" by S. Colonna, A. Manfredi and M. Spadoni.
J. Chem Soc. Perkin Trans. 1, 1995, pp. 1467–1468, "Enantiocomplementary asymmetric epoxidation of selected enones using poly–L–leucine and poly–D–leucine" by M. E. L. Sánchez and S. M. Roberts.
J. Chem. Soc., Perkin Trans. 1, 1997, pp. 3501–3507, "Improved procedure for Juliá–Colonna asymmetric epoxidation of α,β–unsaturated ketones: total synthesis of diltiazem and Taxol™ side–chain" by B. M. Adger et al.

(List continued on next page.)

Primary Examiner—Deborah Lambkin
(74) Attorney, Agent, or Firm—Godfried R. Akorli; Diderico van Eyl

(57) ABSTRACT

The invention relates to a novel process that makes it possible to epoxidize α,β-unsaturated enones or α,β-unsaturated sulfones with high conversions and enantiomeric excesses in the presence of a water-soluble base, an oxidant, water, an organic solvent that is immiscible or has only limited miscibility with water, a preactivated diastereomer- and enantiomer-enriched homo-polyamino acid as catalyst, and a specific phase-transfer catalyst as cocatalyst.

22 Claims, No Drawings

OTHER PUBLICATIONS

Tetrahedron Letters, 42, 2001, pp. 3741–3743, "Asymmetric epoxidation of a geminally–disubstituted and some trisubstituted enones catalysed by poly–L–leucine" by P. A. Bentley, J. F. Bickley, S. M. Roberts and A. Steiner.

Chem. Commun., 1997, pp. 739–740, "Asymmetric epoxidation of enones employing polymeric α–amino acids in non–aqueous media" by P. A. Bentley et al.

Chirality 9: pp. 198–202, 1997, "Preparation of Polyamino Acid Catalysts for Use in Juliá Asymmetric Epoxidation" by P. A. Bentley et al.

Chem. Commun., 1998, pp. 1159–1160, "New procedures for the Juliá–Colonna asymmetric epoxidation: synthesis of (+)–clausenamide" by M. W. Cappi et al.

Tetrahedron: Asymmetry, vol. 8, No. 19, pp. 3163–3173, 1997, Synthetic applications of polymeric α–amino acids by S. Ebrahim and M. Wills.

J. Org. Chem., 1993, 58, pp. 6247–6254, "A Practical, Enantioselective Synthesis of SK&F 104353" by J. R. Flisak et al.

Agnew. Chem. Int. Ed. Engl. 19, 1980, No. 11, "Synthetic Enzymes". Highly Stereoselective Epoxidation of Chalcone in a Triphasic Toluene–Water–Poly[(S)–alanine] System by S. Juliá, J. Masana, and J. C. Vega.

Tetrahedron Letters, 39, 1998, pp. 9297–9300, "Towards a Mechanistic Insight into the Juliá–Colonna Asymmetric Epoxidation of α,β–Unsaturated Ketones Using Discrete Lengths of Poly–leucine." by P. A. Bentley et al.

Baures P. W. et al: "An efficient asymmetric synthesis of substituted phenyl glycidic esters" Tetrahedron Letters., Bd. 31, Nr. 45, 1990, Seiten 6501–6504, XP002006755, Elsevier Science Publishers, Amsterdam., NL ISSN: 0040–4039 das ganze Dokument.

Dhanda, Anupma et al: "PaaSiCats: Novel polyamino acid catalysts" Chirality (2000), 12(5/6), 313–317, XP008009815, das ganze Dokument.

Flood R. W. et al: "Efficient asymmetric epoxidation of alpha, beta–unsaturated ketones using a soluble triblock polyethyleneglycol–polyamino acid catalyst" Organic Letters., Bd. 3, Nr. 5, 8. Marz 2001 (Mar. 8, 2001), Seiten 683–686, XP002219131 ACS, Washington, DC., US ISSN: 1523–7060 das ganze Dokument.

\* cited by examiner

POLYAMINO ACID-CATALYZED PROCESS FOR THE ENANTIOSELECTIVE EPOXIDATION OF α,β-UNSATURATED ENONES AND α,β-UNSATURATED SULFONES

BACKGROUND OF THE INVENTION

The invention relates to a novel process for the enantioselective epoxidation of α,β-unsaturated enones and α,β-unsaturated sulfones using specific polyamino acids as catalysts and phase-transfer catalysts as cocatalysts.

Chiral, nonracemic epoxides are known as valuable synthons for preparing optically active drugs and materials (for example, (a) *Bioorg. Med. Chem.*, 1999, 7, 2145-2156; and (b) *Tetrahedron Lett.*, 1999, 40, 5421–5424). These epoxides can be prepared by enantioselective epoxidation of double bonds. In this case, two stereocenters are produced in one synthetic step. It is therefore not surprising that a large number of methods have been developed for the enantioselective epoxidation of double bonds. However, there is still a great need for novel, improved methods for enantioselective epoxidation.

The epoxidation methods limited to the specific substrates in each case include methods for the enantioselective epoxidation of α,β-unsaturated enones.

Thus, for example, the use of chiral, nonracemic alkaloid-based phase-transfer catalysts for the epoxidation of enones is described in *Tetrahedron Lett.*, 1998, 39, 7563–7566, *Tetrahedron Lett.*, 1998, 39, 1599–1602, and *Tetrahedron Lett.*, 1976, 21, 1831–1834.

*Tetrahedron Lett.*, 1998, 39, 7353–7356, *Tetrahedron Lett.*, 1998, 39, 7321–7322, and *Angew. Chem., Int. Ed. Engl.*, 1997, 36, 410–412, furthermore, describe possibilities for the metal-catalyzed asymmetric epoxidation of enones using organic hydroperoxides.

WO-A 99/52886 describes the possibility of enantioselective epoxidation of enones in the presence of catalysts based on sugars. Another method for epoxidation using Zn organyls and oxygen in the presence of an ephedrine derivative has been published in *Liebigs Ann./Recueil*, 1997, 1101–1113.

*Angew. Chem., Int. Ed. Engl.*, 1980, 19, 929–930, *Tetrahedron*, 1984, 40, 5207–5211, and *J. Chem. Soc., Perkin Trans.* 1, 1982, 1317-24 describe the Juliá epoxidation method in which enantiomer- and diastereomer-enriched polyamino acids are able, in the presence of aqueous hydrogen peroxide and NaOH solution and of an aromatic or halogenated hydrocarbon as solvent, to catalyze the enantioselective epoxidation of α,β-unsaturated enones. Further developments of these so-called three-phase conditions are to be found in *Org. Synth; Mod. Trends, Proc. IUPAC Symp. 6th.*, 1986, 275. The method is now generally referred to as the Juliá-Colonna epoxidation.

According to EP-A 403, 252, it is possible also to employ aliphatic hydrocarbons advantageously in this Juliá-Colonna epoxidation in place of the original solvents.

Furthermore, epoxidation under three-phase conditions has distinct disadvantages. The reaction times under the original conditions are in the region of days even for reactive substrates. For example, 1 to 6 days are required for a trans-chalcone, depending on the polyamino acid used (*Tetrahedron*, 1984, 40, 5207–5211). A preactivation of the polyamino acid carried out in the reaction vessel, by stirring in the solvent with the addition of NaOH solution for 12 to 48 h, shortens the reaction time for many substrates to 1 to 3 days. In this case, no intermediate workup of the catalyst is necessary (EP-A 403, 252). The preactivation can be reduced to a minimum of 6 in the presence of the NaOH/hydrogen peroxide system (*J. Chem. Soc., Perkin Trans.* 1, 1995, 1467–1468).

Despite this improvement, the three-phase method cannot be applied to substrates which are sensitive to hydroxide ions (*J. Chem. Soc., Perkin Trans.* 1, 1997, 3501–3507). A further disadvantage of these classical conditions is that the polyamino acid forms a gel during the reaction (or even during the preactivation). This restricts the required mixing during the reaction and impedes the working up of the reaction mixture.

WO-A 96/33183 describes as a specific embodiment the possibility of carrying out the enantioselective epoxidation of enones also in the presence of the phase-transfer catalyst Aliquat®336 ([(CH$_3$)(C$_8$H$_{17}$)$_3$N$^+$]Cl$^-$) if at the same time a polyamino acid, an organic solvent (such as, for example, dichloromethane), sodium perborate (which is of low solubility in water) as oxidant, and alkali (for example, NaOH) are present. In this context, no more detail is given about the polyamino acid.

*Tetrahedron Lett.*, 2001, 42, 3741-43 merely describes very generally that Aliquat 336 can likewise be added as phase-transfer catalyst (PTC) in the epoxidation of phenyl E-styryl sulfone under conventional three-phase conditions. However, only a slow reaction rate (reaction time 4 days) and a poor enantiomeric excess (21% ee) is achieved. No further information is given about the way this reaction was carried out.

In addition to the original Juliá-Colonna epoxidation under three-phase conditions and the variants mentioned above, other reaction procedures have also been developed. According to *Chem. Commun.*, 1997, 739–740, (pseudo)-anhydrous reaction conditions can be implemented by using THF, 1,2 dimethoxyethane, tert-butyl methyl ether, or ethyl acetate as solvent, a non-nucleophilic base (for example, DBU), and a urea/hydrogen peroxide complex as oxidant. The epoxidation takes place distinctly more quickly under these so-called two-phase reaction conditions. According to *J. Chem. Soc., Perkin Trans.* 1, 1997, 3501–3507, therefore, the enantioselective epoxidation of hydroxide-sensitive enones under the Juliá-Colonna conditions is also possible for the first time in this way.

However, the observation that, on use of the two-phase conditions, the polyamino acid must be preactivated in a separate process in order to achieve rapid reaction times and high enantiomeric excesses proves to be a distinct disadvantage. Several days are needed for this preactivation, which takes place by stirring the polyamino acid in a toluene/NaOH solution. According to *Tetrahedron Lett.*, 1998, 39, 9297–9300, the required preactivated catalyst is then obtained after a washing and drying procedure. This activated polyamino acid forms a paste under the two-phase conditions, which impedes mixing during the reaction and the subsequent workup. According to EP-A 1,006,127, this problem can be solved by adsorbing the activated polyamino acid onto a solid support. Polyamino acids on a silica gel support are referred to as SCATs (silica adsorbed catalysts).

A further disadvantage of the previous two-phase conditions is that the use of relatively costly, non-nucleophilic bases (for example, DBU) is necessary in order to make the reaction possible.

According to EP-A 1,006,111, a further variant of the Juliá-Colonna epoxidation is catalysis of the enantioselective epoxidation by the activated polyamino acid in the presence of water, a water-miscible solvent (for example, 1,2-dimethoxyethane), and sodium percarbonate. The use of water-miscible solvents complicates the workup (extraction) in this process.

In the Juliá-Colonna epoxidation, the reaction rate and the enantiomeric excess (ee) that can be achieved depend greatly on the polyamino acid used and the mode of preparation thereof (*Chirality*, 1997, 9, 198–202). In order to obtain approximately comparable results, a standard system with poly-L-leucine (pII) as catalyst and trans-chalcone as precursor is used throughout for the development and description of novel methods in the literature. However, besides D- or L-polyleucine, other polyamino acids (such as, for example, D- or L-neopentylglycine) are also used successfully (EP-A 1,006,127).

The object of the present invention was to provide a process that makes the polyamino acid-catalyzed enantioselective epoxidation of (α,β-unsaturated enones and α,β-unsaturated sulfones possible but is not subject to the disadvantages of the above-described variants of the Juliá-Colonna epoxidation. It was intended in particular to find a rapid and broadly applicable method that avoids the use of costly bases and oxidants and potentially problematic types of reaction procedure and of workup. At the same time, it was intended that the process have advantages in relation to the space/time yield, handling, economics, and ecology on the industrial scale.

It has now been found, surprisingly, that the epoxidation of α,β-unsaturated enones and α,β-unsaturated sulfones can be carried out under three-phase conditions with substantially shorter reaction times and with, in some cases, distinctly increased enantiomeric excesses when the polyamino acid used as catalyst is preactivated in the presence of a phase-transfer catalyst and, following this, the epoxidation takes place in the presence of this preactivated polyamino acid and of the phase-transfer catalyst.

SUMMARY OF THE INVENTION

The invention thus relates to a process for the epoxidation of α,β-unsaturated enones or α,β-unsaturated sulfones in the presence of
(1) a water-soluble base,
(2) an oxidant,
(3) a diastereomer- and enantiomer-enriched homo-polyamino acid as catalyst,
(4) water,
(5) a solvent that is immiscible or has only limited miscibility with water, and
(6) a phase-transfer catalyst,
wherein the homo-polyamino acid is subjected to a preactivation in the presence of the phase-transfer catalyst before the epoxidation.

DETAILED DESCRIPTION OF THE INVENTION

It is crucial that the process according to the invention be carried out in the presence of a phase-transfer catalyst. It is possible to use, for example, quaternary ammonium salts, quaternary phosphonium salts, onium compounds, or pyridinium salts.

Phase-transfer catalysts that have proved particularly suitable are quaternary ammonium or phosphonium salts of the general formula (I)

$(R^1R^2R^3R^4A)^+X^-$         (I)

where
A is N or P,
$X^-$ is an inorganic or organic anion,
$R^1$ and $R^2$ are identical or different and are alkyl, aryl, aralkyl, cycloalkyl, or heteroaryl radicals that are optionally substituted by one or more identical or different halogen radicals, and
$R^3$ and $R^4$ are identical or different and are alkyl, aryl, aralkyl, cycloalkyl, or heteroaryl radicals that are optionally substituted by one or more identical or different halogen radicals or $R^3$ and $R^4$ together form a $C_4$–$C_6$-cycloalkyl ring with A.

Phase-transfer catalysts of the general formula (I) that have proved suitable are those in which A and $X^-$ have the above-mentioned meanings, and $R^1$, $R^2$, $R^3$, and $R^4$ are identical or different and are $C_1$–$C_{18}$-alkyl, $C_6$–$C_{18}$-aryl, $C_7$–$C_{19}$-aralkyl, $C_5$–$C_7$-cycloalkyl, or $C_3$–$C_{18}$-heteroaryl.

Particularly suitable phase-transfer catalysts are $((C_4H_9)_4N)^+Hal^-$, particularly $((C_4H_9)_4N)^+Br^-$, $((C_4H_9)_4P)^+Hal^-$ (particularly $((C_4H_9)_4P)^+Br^-$), $((C_4H_9)_4N)^+HSO_4^-$, $((C_8H_{17})_4N)^+Br^-$, $[(CH_3)(C_8H_{17})_3N^+]Cl^-$, and $[(CH_3)(C_4H_9)_3N^+]Cl^-$.

X in the general formula (I) is an inorganic or organic cation. $X^-$ is preferably $F^-$, $Cl^-$, $Br^-$, $I^-$, $OH^-$, $HSO_4^-$, $SO_4^-$, $NO_3^-$, $CH_3COO^-$, $CF_3COO^-$, $C_2H_5COO^-$, $C_3H_7COO^-$, $CF_3SO_3^-$, or $C_4F_9SO_3^-$.

The phase-transfer catalysts to be employed according to the invention are normally commercially available or else can be prepared by methods familiar to the skilled person.

The amount of added phase-transfer catalyst is not critical and is normally in the range 0.1 to 20 mol % (preferably in the range 0.5 to 15 mol %, particularly preferably in the range 0.5 to 11 mol %), in each case based on the α, β-unsaturated enones or α,β-unsaturated sulfone employed. However, it is to be observed with amounts that are even lower than 0.1 mol % that the reaction rate decreases markedly, while the high enantiomeric excess is unchanged.

It is possible to employ as α,β-unsaturated enones or α,β-unsaturated sulfones the compounds of the general formula (II)

(II)

in which
X is (C=O) or ($SO_2$), and
$R^5$ and $R^6$ are identical or different and are ($C_1$–$C_{18}$)-alkyl, ($C_2$–$C_{18}$)-alkenyl, ($C_2$–$C_{18}$)-alkynyl, ($C_3$–$C_8$)-cycloalkyl, ($C_6$–$C_{18}$)-aryl, ($C_7$–$C_{19}$)-aralkyl, ($C_1$–$C_{18}$)-heteroaryl or ($C_2$–$C_{19}$)-heteroaralkyl, each of which radicals is optionally substituted once or more than once by identical or different radicals $R^7$, halogen, $NO_2$, $NR^7R^8$, $PO_{0-3}NR^7R^8$, $SO_{0-3}R^7$, $OR^7$, $CO_2R^7$, $CONHR^7$, or $COR^7$, and where optionally one or more $CH_2$ groups in $R^5$ and $R^6$ are replaced by O, $SO_{0-2}$, $NR^7$, or $PO_{0-2}R^7$,
where $R^7$ and $R^8$ are identical or different and are H, ($C_1$–$C_{18}$)-alkyl, ($C_2$–$C_{18}$)-alkenyl, ($C_2$–$C_{18}$)-alkynyl, ($C_3$–$C_8$)-cycloalkyl, ($C_6$–$C_{18}$)-aryl, ($C_1$–$C_{18}$)-heteroaryl, ($C_1$–$C_8$)-alkyl-($C_6$–$C_8$)-aryl, ($C_1$–$C_8$)-alkyl-($C_1$–$C_{19}$)-heteroaryl, or ($C_1$–$C_8$)-alkyl-($C_3$–$C_8$)-cycloalkyl, each of which radicals $R^7$ and $R^8$ is optionally substituted once or more than once by identical or different halogen radicals.

A ($C_1$–$C_{18}$)-alkyl radical means for the purpose of the invention a radical that has 1 to 18 saturated carbon atoms and that may have branches anywhere. It is possible to include in this group in particular the radicals methyl, ethyl, n-propyl, isopropyl, n-butyl, isobutyl, sec-butyl, tert-butyl, pentyl, and hexyl.

A $(C_2-C_{18})$-alkenyl radical has the features mentioned for the $(C_1-C_{18})$-alkyl radical, with the necessity for at least one carbon—carbon double bond to be present within the radical.

A $(C_2-C_{18})$-alkynyl radical has the features mentioned for the $(C_1-C_{18})$-alkyl radical, with the necessity for at least one carbon—carbon triple bond to be present within the radical.

A $(C_3-C_8)$-cycloalkyl radical means a cyclic alkyl radical having 3 to 8 carbon atoms and, where appropriate, a branch anywhere. Included are, particularly, radicals such as cyclopropyl, cyclobutyl, cyclopentyl, cyclo-hexyl, and cycloheptyl. One or more double bonds may be present in this radical.

A $(C_6-C_{18})$-aryl radical means an aromatic radical having 6 to 18 carbon atoms. Included are, particularly, radicals such as phenyl, naphthyl, anthryl, and phenanthryl.

A $(C_7-C_{19})$-aralkyl radical means a $(C_6-C_{18})$-aryl radical linked via a $(C_1-C_8)$-alkyl radical to the molecule.

A $(C_1-C_{18})$-heteroaryl radical designates for the purpose of the invention a five-, six-, or seven-membered aromatic ring system that has 1 to 18 carbon atoms and that has one or more heteroatoms (preferably N, O, or S) in the ring. These heteroaryl radicals include, for example, 2- and 3-furyl, 1-, 2-, and 3-pyrrolyl, 2- and 3-thienyl, 2-, 3-, and 4-pyridyl, 2-, 3-, 4-, 5-, 6-, and 7-indolyl, 3-, 4-, and 5-pyrazolyl, 2-, 4-, and 5-imidazolyl, 1-, 3-, 4-, and 5-triazolyl, 1-, 4-, and 5-tetrazolyl, acridinyl, quinolinyl, phenanthridinyl, 2-, 4-, 5-, and 6-pyrimidinyl and 4-, 5-, 6-, and 7-(1-aza)-indolizinyl.

A $(C_2-C_{19})$-heteroaralkyl radical means a heteroaromatic system corresponding to the $(C_7-C_{19})$-aralkyl radical.

Halogen or Hal means in the context of this invention fluorine, chlorine, bromine, and iodine.

The substrates preferably employed in the process according to the invention are preferably α,β-unsaturated enones or α,β-unsaturated sulfones of the general formula (II) in which $R^5$ and $R^6$ are identical or different and are $(C_1-C_{12})$-alkyl, $(C_2-C_{12})$-alkenyl, $(C_2-C_{12})$-alkynyl, $(C_5-C_8)$-cycloalkyl, $(C_6-C_{12})$-aryl, or $(C_1-C_{12})$-heteroaryl, each of which radicals is optionally substituted once or more than once by identical or different radicals $R^7$, halogen, $NO_2$, $NR^7R^8$, $PO_{0-3}R^7R^8$, or $OR^7$, and $R^7$ and $R^8$ have the meanings indicated above for the general formula (II).

Substrates particularly preferably employed in the process according to the invention are α,β-unsaturated enones or α,β-unsaturated sulfones of the general formula (II) in which $R^5$ and $R^6$ are identical or different and are $(C_1-C_{12})$-alkyl, $(C_2-C_{12})$-alkenyl, $(C_2-C_{12})$-alkynyl, $(C_5-C_8)$-cycloalkyl, $(C_6-C_{12})$-aryl, or $(C_1-C_{12})$-heteroaryl, each of which radicals is optionally substituted once or more than once by identical or different radicals $R^7$, halogen, $NO_2$, $NR^7R^8$, $PO_{0-3}R^7R^8$, or $OR^7$, and $R^7$ and $R^8$ have the meanings indicated above for the general formula (II), with the proviso that at least one of the radicals $R^5$ or $R^6$ is a $(C_2-C_{12})$-alkenyl, $(C_2-C_{12})$-alkynyl, $(C_6-C_{12})$-aryl-, or $(C_1-C_{12})$-heteroaryl radical.

It is particularly preferred to subject substrates of the general formula (III) to the epoxidation according to the invention:

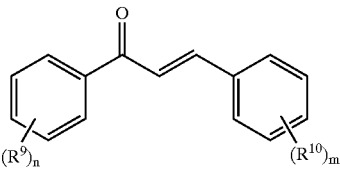

(III)

where
n and m are identical or different and are the numbers 0, 1, 2, or 3,
$R^9$ and $R^{10}$ are identical or different and are $NR^7R^8$, $NO_2$, $OR^7$, $(C_1-C_{12})$-alkyl, $(C_2-C_{12})$-alkenyl, $(C_2-Cl_{12})$-alkynyl, $(C_5-C_8)$-cycloalkyl, $(C_6-C_{12})$-aryl, or $(C_1-C_{12})$-heteroaryl, each of which radicals $R^9$ and $R^{10}$ is optionally substituted once or more than once by identical or different halogen radicals, and
$R^7$ and $R^8$ have the meanings mentioned previously for formula (II).

The process according to the invention for preparing the enantiomer-enriched epoxides is carried out in the presence of homo-polyamino acids, which have previously been subjected to a preactivation in the presence of the phase-transfer catalyst, as catalyst.

It is possible to use for the preactivation a wide variety of diastereomer- and enantiomer-enriched homo-polyamino acids. Preference is given, however, to the use of homo-polyamino acids selected from the group consisting of polyneopentylglycine, polyleucine, polyisoleucine, polyvaline, polyalanine, and polyphenylalanine. The most preferred from this group are polyneopentylglycine and polyleucine.

The chain length of the polyamino acids will be chosen so that, on the one hand, the chiral induction in the reaction is not impaired and, on the other hand, the costs of synthesizing the polyamino acids are not too great. The chain length of the homo-polyamino acids is preferably between 5 and 100 (preferably 7 to 50) amino acids. A chain length of 10 to 40 amino acids is very particularly preferred.

The homo-polyamino acids can be either employed as such unchanged in the preactivation or previously crosslinked with poly-functional amines or chain-extended by other organic polymers. The crosslinking amines advantageously employed for a crosslinking are diaminoalkanes (preferably 1,3-diaminopropane) or crosslinked hydroxy- or aminopolystyrene (CLAMPS, commercially available). Suitable polymer enlargers are preferably nucleophiles based on polyethylene glycol or polystyrene. Polyamino acids modified in this way are described in *Chem. Commun.*, 1998, 1159–1160, and *Tetrahedron: Asymmetry*, 1997, 8, 3163–3173.

For use in the process according to the invention, the homo-polyamino acids are subjected to a preactivation in the presence of a phase-transfer catalyst. For this purpose the polyamino acid, the phase-transfer catalyst, and, normally, the oxidant and the base are suspended in the solvent and stirred for a time in the range from 15 minutes to 2 hours. Either this preactivation can be followed by intermediate isolation of the preactivated homo-polyamino acid or the reaction system can be employed directly in the subsequent epoxidation. In the preactivation the above-mentioned components, base, and oxidant, correspond to those described for the subsequent epoxidation reaction.

The homo-polyamino acids to be employed for the pre-activation can be prepared by state of the art methods (*J. Org. Chem.*, 1993, 58, 6247, and *Chirality*, 1997, 9, 198–202). The method is to be applied to both optical antipodes of the amino acids. The use of a particular antipode of a polyamino acid correlates with the stereochemistry of the epoxide, that is to say a poly-L-amino acid leads to the optical antipode of the epoxide that is obtained with a poly-D-amino acid.

The amount of the homo-polyamino acid employed is not critical and is normally in the range 0.0001 to 40 mol % (preferably in the range 0.001 to 20 mol %, particularly preferably in the range 0.01 to 15 mol %, and especially 1 to 15 mol %), in each case based on the $\alpha,\beta$-unsaturated enone or $\alpha,\beta$-unsaturated sulfone employed.

The oxidants used are, as a rule, peroxides, peracids, or inorganic oxidants such as sodium hypochlorite or sodium percarbonate. Peroxides, peracids, or sodium hypochlorite are preferred. An aqueous $H_2O_2$ solution is particularly preferably employed. This aqueous solution may moreover have all the usual concentrations. Further oxidants to be employed in this reaction are the compounds mentioned in *Methoden Org. Chem.(Houben-Weyl)*, volume 4/1 a+b, 59–319 and the compounds mentioned in *Oxidation in Organic Chemistry*, ACS Monograph 186, Wash. D.C., 1990, 1–47.

The amount of the oxidant employed may be varied within the wide limits of 1 to 40 equivalents. Surprisingly, and advantageously, the reaction according to the invention still takes place with short reaction times and high enantiomeric excesses even with relatively small amounts of oxidant in the range 1 to 10 equivalents, preferably 1 to 3 equivalents, particularly preferably 1.1 to 2.5 equivalents.

The process according to the invention is carried out in the presence of a water-soluble base. It has proved suitable to employ for this purpose alkali metal hydroxides such as NaOH, KOH, or LiOH. The base is normally employed in the form of an aqueous solution.

The amount of the base employed may be varied within the wide limits of 0.1 to 10 equivalents. Surprisingly, and advantageously, the reaction according to the invention still takes place with short reaction times and high enantiomeric excesses even with relatively small amounts of bases in the range 0.5 to 5 equivalents, preferably 0.8 to 2 equivalents.

The process according to the invention is carried out using a solvent that is immiscible or has only limited miscibility with water. A solvent is regarded as having limited miscibility with water in the context of this invention if a mixture of the organic solvent and water at 20° C. can contain no more than 20% by weight (preferably not more than 10% by weight, and in particular not more than 8% by weight) of water in order to remain a single phase.

Suitable organic solvents are in general unsubstituted or substituted aromatic hydrocarbons, aliphatic hydrocarbons, haloalkanes, and ethers. Particularly suitable are toluene, xylene, hexane, tert-butyl methyl ether, diethyl ether, chloroform, and methylene chloride.

It has been found that the homo-polyamino acid pII aggregates in tert-butyl methyl ether. Hence tert-butyl methyl ether is an interesting and suitable solvent for a continuous reaction procedure.

The temperature used in the epoxidation is generally in the range from −10 to +50° C., preferably in the range from 0 to +40° C., and particularly at +10 to +30° C.

The pH set during the reaction can be chosen so that an excess of deprotonated $H_2O_2$ is present compared with nondeprotonated $H_2O_2$. On the other hand, the pH in the reaction should also not be chosen so high as to harm the organic compounds employed. The pH is preferably in the range 7 to 14, preferably in the range 7.5 to 13.

The water content of the system normally results from the fact that, as previously described, individual reaction components of the system, such as the base and the oxidant, are employed in the form of aqueous solutions. The total water content in the reaction mixture is in the range 1 to 70% by weight (preferably in the range 5 to 50% by weight), based on the complete reaction mixture.

The procedure for preactivation of the homo-polyamino acid is normally carried out in such a way that, apart from the substrate to be epoxidized, all the reaction components of the process—that is to say homo-polyamino acid, phase-transfer catalyst, base, oxidant and solvent—are mixed. This mixture is then stirred for a period of from 15 minutes to 2 hours. Either this preactivation can be followed by intermediate isolation of the preactivated homo-polyamino acid or preferably the reaction system can be employed directly in the subsequent epoxidation, that is to say the substrate added. In the case of intermediate isolation, the homo-polyamino acid is removed from the reaction mixture (for example, by centrifugation), washed with water until neutral, washed with acetone, and dried.

The process according to the invention is distinguished by greatly reduced reaction times. Instead of requiring days, epoxidation of the $\alpha,\beta$-unsaturated enones and of the $\alpha,\beta$-unsaturated sulfones can be achieved with high conversion and high enantioselectivity in only a few hours or even only minutes.

The process according to the invention avoids the very elaborate preparation, necessary in the prior art, of the activated homo-polyamino acids over a period of several days through the addition of a phase-transfer catalyst. In the presence of such a phase-transfer catalyst the activation of the homo-polyamino acid takes place within minutes or a maximum of 2 hours, whereas under the original three-phase conditions a minimum of 6 hours, and under the two-phase, the SCAT, and the percarbonate conditions 4 to 5 days are required. Intermediate isolation of the preactivated homo-polyamino acid is (in contrast to the two-phase, the SCAT, and the percarbonate conditions) unnecessary.

The use according to the invention of the phase-transfer catalyst as cocatalyst additionally permits the necessary amount of oxidant and of base to be reduced markedly without having an adverse effect on reaction rate, conversion or enantiomeric excess. In addition, particularly low-cost bases and oxidants can be employed.

Because of the very short reaction times, for the first time hydroxide-sensitive substrates, which cannot be successfully epoxidized by the conventional three-phase conditions (*JCS., Perkin Trans.* 1, 1997, 3501–3507), are also amenable to enantioselective epoxidation via the process according to the invention.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

The process for preparing polyamino acids often provides catalysts for the Julia-Colonna epoxidation that vary widely in catalytic activity (*Chirality*, 1997, 9, 198–202). The conversion per unit time and the enantiomeric excess can be compared for a particular substrate only if the same polyamino acid batch is used for the epoxidation reaction.

For this reason, direct comparison of new results with results published in the literature is impossible, simply because different catalyst batches are inevitably used. For this reason, uniform polyleucine batches were used in each of the subsequent example groups I to V (both in the examples according to the invention and in the corresponding comparative examples).

In all the following examples, the conversion and the enantiomeric excess (ee) were determined by methods known from the literature using HPLC on a chiral, nonracemic phase (UV detection).

Example Group I

Examples 1 and 2 and Comparative Examples CE 3 and 4
Epoxidation of trans-chalcone (1) to epoxychalcone (2)

Scheme 1:

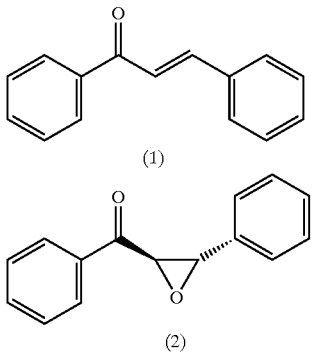

(1)

(2)

Examples 1 and 2
3-Phase Conditions with PTC and with pII Preactivation 100 mg of non-preactivated pII and 8.5 mg of $(Bu_4N)^+Br^-$ (Example 1) or 11 mg of Aliquat 336 (Example 2) were suspended in a mixture of 0.8 ml of toluene and 62 $\mu$l of NaOH (employed as 5 molar aqueous solution, corresponding to 1.3 equivalents). Then 32 $\mu$l of $H_2O_2$ (employed as 30% strength aqueous solution, corresponding to 1.3 equivalents) were added. This mixture was stirred at room temperature for 1.5 hours for preactivation of the pII.

Subsequently, 50 mg of trans-chalcone were added and the reaction mixture was stirred for a reaction time of 10 min. This was followed by dilution of the reaction mixture with 2 ml of ethyl acetate and subsequent slow introduction into a stirred, ice-cold aqueous $NaHSO_3$ solution (4 ml, 20% strength). After centrifugation, the supernatant was dried over sodium sulfate and concentrated under reduced pressure.

Comparative Examples CE 3 and 4
3-Phase Conditions with PTC Without pII Preactivation 100 mg of non-preactivated pII, 50 mg of trans-chalcone, and 8.5 mg of $(Bu_4N)^+Br^-$ (Comparative Example 3) or 11 mg of Aliquat ® 336 (Comparative Example 4) were suspended in a mixture of 0.8 ml of toluene and 62 $\mu$l of NaOH (employed as 5 molar aqueous solution, corresponding to 1.3 equivalents). Then 32 $\mu$l of $H_2O_2$ (employed as 30% strength aqueous solution, 1.3 equivalents) were added. This mixture was allowed to react at room temperature with stirring. After a reaction time of 10 min, the reaction mixture was diluted with 2 ml of ethyl acetate and then slowly introduced into a stirred, ice-cold aqueous $NaHSO_3$ solution (4 ml, 20% strength). After centrifugation, the supernatant was dried over sodium sulfate and concentrated under reduced pressure.

The results of Examples 1 and 2 and of Comparative Examples CE 3 and 4 are summarized in Table 1 below.

TABLE 1

| Example | PTC | Reaction time [min] | Conversion [%] | ee [%] |
|---|---|---|---|---|
| 1 | $(Bu_4N)^+Br^-$ | 10 | 97 | 95 |
| 2 | Aliquat ® 336 | 10 | 74 | 94 |
| CE 3 | $(Bu_4N)^+Br^-$ | 10 | 97 | 94 |
| CE 4 | Aliquat ® 336 | 10 | 67 | 89 |

Example Group II

Examples 5 and 6 and Comparative Examples CE 7 and 8
Epoxidation of trans-aminochalcone (3) to (4)

Scheme 2:

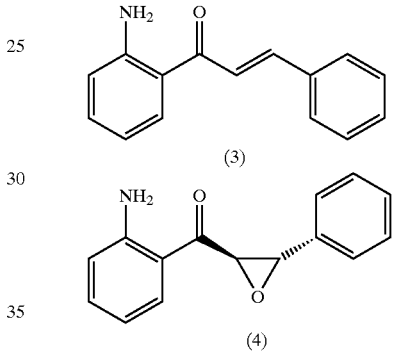

(3)

(4)

Examples 5 and 6
3-Phase Conditions with PTC and with pII Preactivation 100 mg of non-preactivated pII and 8.5 mg of $(Bu_4N)^+Br^-$ (or 10.8 mg Aliquat® 336) were suspended in a mixture of 0.8 ml of toluene and 200 $\mu$l of NaOH (employed as 5 molar aqueous solution, corresponding to 4.2 equivalents). Then 125 $\mu$l of $H_2O_2$ (employed as 30% strength aqueous solution, corresponding to 5.0 equivalents) were added. This mixture was stirred at room temperature for 1.5 hours for the purpose of preactivating the pII.

Subsequently, 54 mg of trans-aminochalcone were added and the reaction mixture was stirred for 30 min. The reaction mixture was then diluted with 2 ml of ethyl acetate and introduced slowly into a stirred, ice-cold aqueous $NaHSO_3$ solution (4 ml, 20% strength). After filtration, the organic phase of the filtrate was dried over sodium sulfate and concentrated under reduced pressure.

Comparative Examples CE 7 and 8
3-Phase Conditions with PTC Without pII Preactivation 100 mg of non-preactivated pII, 54 mg of trans-aminochalcone and 8.5 mg of $(Bu_4N)^+Br^-$ (or 10.8 mg of Aliquat 336) were suspended in a mixture of 0.8 ml of toluene and 200 $\mu$l of NaOH (employed as 5 molar aqueous solution, corresponding to 4.2 equivalents). Then 125 $\mu$l of $H_2O_2$ (employed as 30% strength aqueous solution, corresponding to 5.0 equivalents) were added. This mixture was allowed to react at room temperature with stirring. After a reaction time of 30 min, the reaction mixture was diluted with 2 ml of ethyl acetate and then slowly introduced into a stirred, ice-cold aqueous NaHSO₃ solution (4 ml, 20% strength). After filtration, the organic phase of the filtrate was dried over sodium sulfate and concentrated under reduced pressure.

The results of Examples 5 and 6 and of Comparative Examples CE 7 and 8 are summarized in Table 2 below.

TABLE 2

| Example | PTC | Reaction time [min] | Conversion [%] | ee [%] |
|---|---|---|---|---|
| 5 | (Bu₄N)⁺Br⁻ | 30 | 100 | 92 |
| 6 | Aliquat ® 336 | 30 | 100 | 91 |
| CE 7 | (Bu₄N)⁺Br⁻ | 30 | 89 | 87 |
| CE 8 | Aliquat ® 336 | 30 | 74 | 55 |

Example Group III

Examples 9 and 10 and Comparative Examples CE 11 and 12
Epoxidation of phenyl trans-styryl sulfone (5) to (6)

Scheme 3:

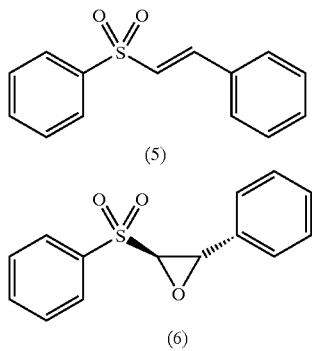

Examples 9 and 10
3-Phase Conditions with PTC and with pII Preactivation 100 mg of non-preactivated pII and 8.5 mg of (BU₄N)⁺Br⁻ (Example 9) or 11 mg of Aliquat 336 (Example 10) were suspended in a mixture of 0.8 ml of toluene and 200 μl of NaOH (employed as 5 molar aqueous solution, corresponding to 4.2 equivalents). Then 120 μl of H₂O₂ (employed as 30% strength aqueous solution, corresponding to 5 equivalents) were added. This mixture was stirred at room temperature for 1.5 hours for preactivation of the pII.

Subsequently, 59 mg of phenyl trans-styryl sulfone were then added and stirred for a further 2 hours. The reaction mixture was diluted with 2 ml of ethyl acetate and then centrifuged. The supernatant was then slowly introduced into 2 ml of water. After phase separation, the organic phase was dried over sodium sulfate and concentrated under reduced pressure.

Comparative Examples CE 11 and 12
3-Phase Conditions with PCT Without pII Preactivation 100 mg of non-preactivated pII, 59 mg of phenyl trans-styryl sulfone, and 8.5 mg of (Bu₄N)⁺Br⁻ (CE 11) or 11 mg of Aliquat® 336 (CE 12) were suspended in a mixture of 0.8 ml of toluene and 200 μl of NaOH (employed as 5 molar aqueous solution, corresponding to 4.2 equivalents). Then 125 μl of H₂O₂ (employed as 30% strength aqueous solution, corresponding to 5 equivalents) were added. This mixture was allowed to react at room temperature with stirring. After a reaction time of 2 h, the reaction mixture was diluted with 2 ml of ethyl acetate and then centrifuged. The supernatant was then slowly introduced into 2 ml of water. After phase separation, the organic phase was dried over sodium sulfate and concentrated under reduced pressure.

The results of Examples 9 and 10 and of Comparative Examples CE 11 and 12 are summarized in Table 3 below.

TABLE 3

| Example | PTC | Reaction time [h] | Conversion [%] | ee [%] |
|---|---|---|---|---|
| 9 | (Bu₄N)⁺Br⁻ | 2 | 82 | 68 |
| 10 | Aliquat ® 336 | 2 | 95 | 65 |
| CE 11 | (Bu₄N)⁺Br⁻ | 2 | 79 | 53 |
| CE 12 | Aliquat ® 336 | 2 | 92 | 22 |

Example Group IV

Example 13 and Comparative Example 14
Epoxidation of (E)-1,2-dibenzoylethylene (7) to (8)

Scheme 4:

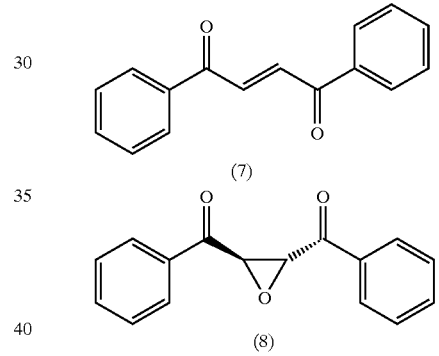

Example 13
3-Phase Conditions with PTC and with Preactivation of pII 100 mg of non-preactivated pII (11 mol %) and 8.5 mg of (Bu₄N)⁺Br⁻ (11 mol %) were suspended in a mixture of 0.8 ml of toluene and 63 μl of NaOH (employed in the form of a 5 molar aqueous solution, corresponding to 1.3 equivalents). Then 32 μl of H₂O₂ (employed in the form of a 30% aqueous solution, corresponding to 1.3 equivalents) were added. This mixture was stirred for 1.5 hours at room temperature for the purpose of preactivating the pII.

Then 57 mg of (E)-1,2-dibenzoylethylene were added and the reaction mixture was stirred for a reaction time of 8 min. The reaction mixture was diluted with 2 ml of ethyl acetate and then introduced slowly into a stirred, ice-cold, aqueous NaHSO₃ solution (4 ml, 20% strength). After filtering off the polymer the organic phase of the filtrate was dried over sodium sulfate and concentrated under reduced pressure. A conversion rate of 100% and an enantiomeric excess of 92% ee were obtained (determined by a shift ¹H-NMR-experiment with Eu(tfc)₃ as the shift reagent).

Comparative Example 14
3-Phase Conditions with PTC Without Preactivation of pII 100 mg of non-preactivated pII (11 mol %), 57 mg of (E)-1,2-dibenzoylethylene and 8.5 mg of (Bu₄N)⁺Br⁻ (11 mol %) were suspended in a mixture of 0.8 ml of toluene and 63 μl, of NaOH (employed in the form of a 5 molar aqueous solution, corresponding to 1.3 equivalents). Then 32 μl of H₂O₂ (employed in the form of a 30% strength aqueous solution, corresponding to 1.3 equivalents) were added. This mixture was allowed to react with stirring at room temperature. After a reaction time of 8 min the reaction mixture was diluted with 2 ml of ethyl acetate and then introduced slowly into a stirred, ice-cold, aqueous NaHSO₃ solution (4 ml, 20% strength). After filtering off the polymer, the organic phase of the filtrate was dried over sodium sulfate and concentrated under reduced pressure. A conversion rate of 100% and an enantiomeric excess of 69% ee were obtained (determined by a shift ¹H-NMR experiment with Eu(tfc)₃ as the shift reagent).

Example Group V

Example 15 and Comparative Example 16

Epoxidation of (E)-1,2-dibenzoylethylene (7) to (8) According to Scheme 4

Example 15

3-Phase Conditions with PTC and with Preactivation of pII 100 mg of non-preactivated pII (11 mol %) and 14.5 mg of (Oct₄N)⁺Br⁻ (11 mol %) were suspended in a mixture of 0.8 ml of toluene and 63 ∥l of NaOH (employed in the form of a 5 molar aqueous solution, corresponding to 1.3 equivalents). Then 32 μl of H₂O₂ (employed in the form of a 30% strength aqueous solution, corresponding to 1.3 equivalents) were added. This mixture was stirred for 1.5 hours at room temperature for the purpose of preactivating the p ll.

Then 57 mg of (E)-1,2-dibenzoylethylene were added and the reaction mixture was stirred for a reaction time of 15 min. The reaction mixture was diluted with 2 ml of ethyl acetate and then introduced slowly into a stirred, ice-cold, aqueous NaHSO₃ solution (4 ml, 20% strength). After filtering off the polymer, the organic phase of the filtrate was dried over sodium sulfate and concentrated under reduced pressure. A conversion rate of 100% and an enantiomeric excess of 95% ee were obtained (determined by a shift ¹H-NMR experiment with Eu(tfc)₃ as the shift reagent).

Comparative Example 16

3-Phase Conditions with PTC Without Preactivation of pII 100 mg of non-preactivated pII (11 mol %), 57 mg of (E)-1,2-diben-zoylethylene, and 14.5 mg of (Oct₄N)⁺Br⁻ (11 mol %) were suspended in a mixture of 0.8 ml of toluene and 63 μl of NaOH (employed as a 5 molar aqueous solution, corresponding to 1.3 equivalents). Then 32 μl of H₂O₂ (employed in the form of a 30% strength, aqueous solution, corresponding to 1.3 equivalents) were added. This mixture was allowed to react with stirring at room temperature. After a reaction time of 15 min, the reaction mixture was diluted with 2 ml of ethyl acetate and then introduced slowly into a stirred, ice-cold, aqueous NaHSO₃ solution (4 ml, 20% strength). After filtering off the polymer, the organic phase of the filtrate was dried over sodium sulfate and concentrated under reduced pressure. A conversion rate of 100% and an enantiomeric excess of 82% ee were obtained (determined by a shift ¹H-NMR-experiment with Eu(tfc)₃ as the shift reagent).

Example 17

Epoxidation of benzylidene acetone (11) to (12) (Three-Phase Conditions with PTC and with Preactivation)

Scheme 5:

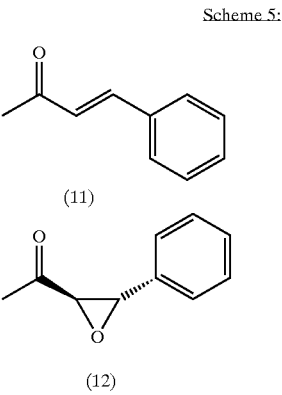

200 mg of non-preactivated pII (11 mol %) and 17 mg of (Bu₄N)⁺Br⁻ (11 mol %) were suspended in a mixture of 1.6 ml of toluene and 0.4 ml of NaOH (employed in the form of a 5 molar aqueous solution, corresponding to 4.2 equivalents). Then 0.25 ml of H₂O₂ (employed as a 30% strength aqueous solution, corresponding to 5.0 equivalents) were added. This mixture was stirred for 1.5 hours at room temperature for the purpose of preactivating the pII.

Then 70 mg of benzylidene acetone were added and the reaction mixture was stirred for a reaction time of 1 hour. The reaction mixture was diluted with 2 ml of ethyl acetate and then centrifuged. The supernatant was then introduced slowly into 2 ml of water. After phase separation, the organic phase was dried over sodium sulfate and concentrated under reduced pressure. A yield of 64% and an enantiomeric excess of 77% ee (determined by a shift ¹H-NMR experiment) were obtained at a conversion rate of 83%.

What is claimed is:

1. A process comprising epoxidizing α,β-unsaturated enones or α,β-unsaturated sulfones in the presence of
   (1) a water-soluble base,
   (2) an oxidant,
   (3) a diastereomer- and enantiomer-enriched homo-polyamino acid as catalyst,
   (4) water,
   (5) a solvent that is immiscible or has only limited miscibility with water, and
   (6) a phase-transfer catalyst,
   wherein the homo-polyamino acid is subjected to a preactivation in the presence of the phase-transfer catalyst before the epoxidation.

2. A process according to claim 1 wherein the phase-transfer catalyst is a quaternary ammonium salt, quaternary phosphonium salt, onium compound, or pyridinium salt.

3. A process according to claim 2 wherein the phase-transfer catalyst is a quaternary ammonium or phosphonium salt of the formula (I)

$$(R^1R^2R^3R^4A)^+X^-$$  (I)

where
   A is N or P,
   X⁻ is an inorganic or organic anion,
   R¹ and R² are identical or different and are alkyl, aryl, aralkyl, cycloalkyl or heteroaryl radicals that are optionally substituted by one or more identical or different halogen radicals, and R³ and R⁴ are identical or different and are alkyl, aryl, aralkyl, cycloalkyl, or heteroaryl radicals that are optionally substituted by one or more identical or different halogen radicals or R³ and R⁴ together form a $C_4$–$C_6$-cycloalkyl ring with A.

4. A process according to claim 3 wherein X⁻ is F⁻, Cl⁻, Br⁻, I⁻, OH⁻, $NO_3^-$, $HSO_4^-$, $SO_4^-$, $CH_3COO^-$, $CF_3COO^-$, $C_2H_5COO^-$, $C_3H_7COO^-$, $CF_3SO_3^-$, or $C_4F_9SO_3^-$.

5. A process according to claim 3 wherein, for the phase-transfer catalysts of the formula (I), R¹, R², R³, and R⁴ are identical or different and are $C_1$–$C_{18}$-alkyl, $C_6$–$C_{18}$-aryl, $C_7$–$C_{19}$-aralkyl, $C_5$–$C_7$-cycloalkyl or $C_3$–$C_{18}$-heteroaryl.

6. A process according to claim 3 wherein the phase-transfer catalyst is $((C_4H_9)_4N)^+Hal^-$, $((C_4H_9)_4P)^+Hal^-$, $((C_4H_9)_4N)^+HSO_4^-$ $((C_8H_{17})_4N^+Br^-$, $[(CH_3)(C_8H_{17})_3N]^+Cl^-$, or $[(CH_3)(C_4H_9)_3N]^+Cl^-$.

7. A process according to claim 1 wherein the phase-transfer catalyst is employed in an amount in the range 0.1 to 20 mol %, based on the α,β-unsaturated enone or α,β-unsaturated sulfone.

8. A process according to claim 1 wherein the α,β-unsaturated enones or α,β-unsaturated sulfones have the formula (II)

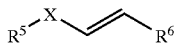

(II)

in which

X is (C=O) or ($SO_2$), and

R⁵ and R⁶ are identical or different and are ($C_1$–$C_{18}$)-alkyl, ($C_2$–$C_{18}$)-alkenyl, ($C_2$–$C_{18}$)-alkynyl, ($C_3$–$C_8$)-cycloalkyl, ($C_6$–$C_{18}$)-aryl, ($C_7$–$C_{19}$)-aralkyl, ($C_1$–$C_{18}$)-heteroaryl, or ($C_2$–$C_{19}$)-heteroaralkyl, each of which radicals is optionally substituted once or more than once by identical or different radicals R⁷, halogen, $NO_2$, $NR^7R^8$, $P_{0-3}R^7R^8$, $SO_{0-3}R^7$, $OR^7$, $CO_2R^7$, $CONHR^7$, or $COR^7$, and where optionally one or more $CH_2$ groups in R⁵ and R⁶ are replaced by O, $SO_{0-2}$, $NR^7$, or $PO_{0-2}R^7$, where R⁷ and R⁸ are identical or different and are H, ($C_1$–$C_{18}$)-alkyl, ($C_2$–$C_{18}$)-alkenyl, ($C_2$–$C_{18}$)-alkynyl, ($C_3$–$C_8$)-cycloalkyl, ($C_6$–$C_{18}$)-aryl, ($C_1$–$C_{18}$)-heteroaryl, ($C_1$–$C_8$)-alkyl-($C_6$–$C_8$)-aryl, ($C_1$–$C_8$)-alkyl-($C_1$–$C_{18}$)-heteroaryl, or ($C_1$–$C_8$)-alkyl-($C_3$–$C_8$)-cycloalkyl, each of which radicals R⁷ and R⁸ is optionally substituted once or more than once by identical or different halogen radicals.

9. A process according to claim 1 wherein the α,β-unsaturated enones or (α,β-unsaturated sulfones have the formula (II)

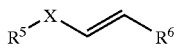

(II)

in which

X is (C=O) or ($SO_2$),

R⁵ and R⁶ are identical or different and are ($C_1$–$C_{12}$)-alkyl, ($C_2$–$C_{12}$)-alkenyl, ($C_2$–$C_{12}$)-alkynyl, ($C_5$–$C_8$)-cycloalkyl, ($C_6$–$C_{12}$)-aryl, or ($C_1$–$C_{12}$)-heteroaryl, each of which radicals is optionally substituted once or more than once by identical or different radicals R⁷, halogen, $NO_2$, $NR^7R^8$, $PO_{0-3}R^7R^8$, or $OR^7$, and R⁷ and R⁸ are identical or different and are H, ($C_1$–$C_{18}$)-alkyl, ($C_2$–$C_{18}$)-alkenyl, ($C_2$–$C_{18}$)-alkynyl, ($C_3$–$C_8$)-cycloalkyl, ($C_6$–$C_{18}$)-aryl, ($C_1$–$C_{18}$)-heteroaryl, ($C_1$–$C_8$)-alkyl-($C_6$–$C_8$)-aryl, ($C_1$–$C_8$)-alkyl-($C_1$–$C_{18}$)-heteroaryl, or ($C_1$–$C_8$)-alkyl-($C_3$–$C_8$)-cycloalkyl, each of which radicals R⁷ and R⁸ is optionally substituted once or more than once by identical or different halogen radicals.

10. A process according to claim 1 wherein the α,β-unsaturated enones or α,β-unsaturated sulfones are compounds of the formula (II)

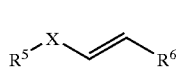

(II)

in which

X is (C=O) or ($SO_2$), and

R⁵ and R⁶ are identical or different and are ($C_1$–$C_{12}$)-alkyl, ($C_2$–$C_{12}$)-alkenyl, ($C_2$–$C_{12}$)-alkynyl, ($C_5$–$C_8$)-cycloalkyl, ($C_6$–$C_{12}$)-aryl, or ($C_1$–$C_{12}$)-heteroaryl, each of which radicals is optionally substituted once or more than once by identical or different radicals R⁷, halogen, $NO_2$, $NR^7R^8$, $PO_{0-3}R^7R^8$, or $OR^7$, and R⁷ and R⁸ are identical or different and are H, ($C_1$–$C_{18}$)-alkyl, ($C_2$–$C_{18}$)-alkenyl, ($C_2$–$C_{18}$)-alkynyl, ($C_3$–$C_8$)-cycloalkyl, ($C_6$–$C_{18}$)-aryl, ($C_1$–$C_{18}$)-heteroaryl, ($C_1$–$C_8$)-alkyl-($C_6$–$C_8$)-aryl, ($C_1$–$C_8$)-alkyl-($C_1$–$C_{18}$)-heteroaryl, or ($C_1$–$C_8$)-alkyl-($C_3$–$C_8$)-cycloalkyl, each of which radicals R⁷ and R⁸ is optionally substituted once or more than once by identical or different halogen radicals, with the proviso that at least one of the radicals R⁵ or R⁶ is a ($C_2$–$C_{12}$)-alkenyl, alkenyl, ($C_2$–$C_{12}$)-alkynyl, ($C_6$–$C_{12}$)-aryl-, or ($C_1$–$C_{12}$)-heteroaryl radical.

11. A process according to claim 1 wherein the α,β-unsaturated enones or α,β-unsaturated sulfones are compounds of the formula (III)

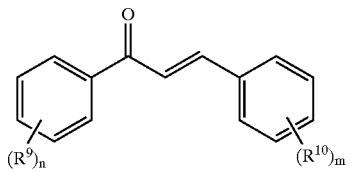

(III)

where n and m are identical or different and are the numbers 0, 1, 2, or 3,

R⁹ and R¹⁰ are identical or different and are $NR^7R^8$, $NO_2$, $OR^7$, ($C_1$–$C_{12}$)-alkyl, ($C_2$–$C_{12}$)-alkenyl, ($C_2$–$C_{12}$)-alkynyl, ($C_5$–$C_8$)-cycloalkyl, ($C_6$–$C_{12}$)-aryl, or ($C_1$–$C_1$)-heteroaryl, each of which radicals R⁹ and R¹⁰ is optionally substituted once or more than once by identical or different halogen radicals, and R₇ and R⁸ are identical or different and are H, ($C_1$–$C_{18}$)-alkyl, ($C_2$–$C_{18}$)-alkenyl, ($C_2$–$C_{18}$)-alkynyl, ($C_3$–$C_8$)-cycloalkyl, ($C_6$–$C_{18}$)-aryl, ($C_1$–$C_{18}$)-heteroaryl, ($C_1$–$C_8$)-alkyl-($C_6$–$C_8$)-aryl, ($C_1$–$C_8$)-alkyl-($C_1$–$C_{18}$)-heteroaryl, or ($C_1$–$C_8$)-alkyl-($C_3$–$C_8$)-cycloalkyl, each of which radicals R⁷ and R⁸ is optionally substituted once or more than once by identical or different halogen radicals.

12. A process according to claim 1 wherein the diastereomer- and enantiomer-enriched homo-polyamino acids are selected from the group consisting of polyneopentylglycine, polyleucine, polyisoleucine, polyvaline, polyalanine, and polyphenylalanine.

13. A process according to claim 1 wherein the polyamino acid has a chain length in the range from 5 to 100 amino acid repeating units.

14. A process according to claim 1 wherein the homopolyamino acids are for preactivation suspended together with the phase-transfer catalyst in the presence of the base and of the oxidant in an organic solvent and stirred for a time of from 15 minutes to 2 hours and either then undergoes intermediate isolation or is used directly as a reaction system for the epoxidation after addition of the α,β-unsaturated enone or α,β-unsaturated sulfone.

15. A process according to claim 1 wherein the homopolyamino acid is employed in the range 0.1 to 40 mol %, based on the (α,β-unsaturated enone or α,β-unsaturated sulfone.

16. A process according to claim 1 wherein the oxidant is a peroxide, peracid, or inorganic oxidant.

17. A process according to claim 1 wherein the oxidant is an aqueous $H_2O_2$ solution.

18. A process according to claim 1 wherein 1 to 40 equivalents of the oxidant is employed.

19. A process according to claim 1 wherein the water-soluble base is an alkali metal hydroxide.

20. A process according to claim 1 wherein 0.1 to 10 equivalents of the base is employed.

21. A process according to claim 1 wherein the organic solvent is an unsubstituted or substituted aromatic hydrocarbon, aliphatic hydrocarbon, haloalkane, or ether.

22. A process according to claim 1 wherein the reaction temperature is in the range from −10 to +50° C.

* * * * *